US008876737B2

(12) United States Patent
Behan et al.

(10) Patent No.: US 8,876,737 B2
(45) Date of Patent: Nov. 4, 2014

(54) MONITORING SLEEP STAGES TO DETERMINE OPTIMAL AROUSAL TIMES AND TO ALERT AN INDIVIDUAL TO NEGATIVE STATES OF WAKEFULNESS

(75) Inventors: Julie Behan, Shanagolden (IE); David Prendergast, Summerhill (IE)

(73) Assignee: Intel-GE Care Innovations LLC, Roseville, CA (US)

( * ) Notice: Subject to any disclaimer, the term of this patent is extended or adjusted under 35 U.S.C. 154(b) by 1237 days.

(21) Appl. No.: 12/335,086

(22) Filed: Dec. 15, 2008

(65) Prior Publication Data

US 2010/0152546 A1    Jun. 17, 2010

(51) Int. Cl.
*A61B 5/103*    (2006.01)
*A61B 5/00*    (2006.01)
*A61B 5/11*    (2006.01)

(52) U.S. Cl.
CPC ............ *A61B 5/1118* (2013.01); *A61B 5/6887* (2013.01); *A61B 5/4812* (2013.01); *A61B 5/4809* (2013.01); *A61B 5/0002* (2013.01)
USPC .......................................... 600/595; 340/575

(58) Field of Classification Search
USPC .......................................... 600/595; 340/575
See application file for complete search history.

(56) References Cited

U.S. PATENT DOCUMENTS

| 6,544,200 | B1* | 4/2003 | Smith et al. ................... 600/595 |
| 7,956,756 | B2* | 6/2011 | Kubey et al. .................. 340/575 |
| 2005/0012622 | A1* | 1/2005 | Sutton ........................ 340/573.1 |
| 2006/0055543 | A1* | 3/2006 | Ganesh et al. ............. 340/573.1 |
| 2008/0157956 | A1* | 7/2008 | Radivojevic et al. ......... 340/531 |
| 2008/0172789 | A1* | 7/2008 | Elliot et al. ....................... 5/616 |

OTHER PUBLICATIONS

C.N. Scanaill et al., "A Review of Approaches to Mobility Telemonitoring of the Elderly in Their Living Environment", Annals of Biomedical Engineering, vol. 34, No. 4, Apr. 2006.

* cited by examiner

*Primary Examiner* — Max Hindenburg
*Assistant Examiner* — Renee Danega
(74) *Attorney, Agent, or Firm* — Pillsbury Winthrop Shaw Pittman LLP

(57) ABSTRACT

A system and method for monitoring sleep stages to determine optimal arousal times and to alert an individual to negative states of wakefulness. In an embodiment, a device receives pressure data from at least one pressure sensor, where the pressure sensor is associated with furniture used for an individual to sleep. The device uses the pressure data to determine a sleep stage for the individual. The sleep stage is used to determine whether it is an optimal arousal time for the individual. The device sends an indication to not wake the individual if it is not the optimal arousal time for the individual. Other embodiments are described and claimed.

26 Claims, 10 Drawing Sheets

MONITORING SLEEP STAGES TO DETERMINE OPTIMAL AROUSAL TIMES AND TO ALERT AN INDIVIDUAL TO NEGATIVE STATES OF WAKEFULNESS

BACKGROUND

A night's sleep consists of a series of sleep cycles each lasting 90-110 minutes in duration, with an average adult experiencing 4-5 of these cycles each night. A typical sleep cycle has five stages, which may be further categorized into non-rapid eye movement (NREM) and rapid eye movement (REM) sleep stages. NREM and REM sleep stages may be identified through physiological patterns.

There are four stages of NREM sleep. The lighter stages of NREM sleep appear first (stages 1 and 2), and often alternate with brief episodes of wakefulness before the deeper NREM stages are entered (stages 3 and 4). The REM sleep stage appears at around 90 minute intervals. As the night progresses the REM sleep stages become longer and NREM sleep stages become both shorter and lighter. Brief arousals to wakefulness are a normal feature of sleep.

The stages of sleep offer different benefits to the sleeper. REM sleep, or dream sleep, is essential to our minds for processing and consolidating emotions, memories and stress. It is also thought to be vital to learning, stimulating the brain regions used in learning and developing new skills. Most of dreaming occurs during REM sleep, although it can happen during other sleep stages as well. If REM sleep is disrupted one night, your body will go through more REM sleep the next night to catch up on this sleep stage. This may be an indication of the importance of REM sleep. However, deep sleep (stages 3 and 4 of NREM sleep) is perhaps the most vital stage. It is the first stage that the brain attempts to recover when sleep deprived, and the strongest effects of sleep deprivation are from inadequate deep sleep. Thus, getting adequate deep sleep (stages 3 and 4 of NREM sleep) and REM sleep should be encouraged.

A person is likely to have different experiences when awakening from each of the sleep stages. For example, the highest arousal thresholds (e.g., difficulty of awakening) are observed in NREM sleep stages 4 and 3 (deep sleep), respectively. Intrusion of wakefulness from stages 3 and 4 of NREM sleep is characteristic of "disorders of arousal". Here, the transitions from stages 3 and 4 of NREM sleep to wakefulness are incomplete or gradual and features of both states coexist temporarily. The commonest and mildest example of this is sleep inertia, in which sleep is followed by drowsiness or at least a sensation of feeling un-refreshed and of being no more alert after sleep than beforehand. Sleep inertia is often accompanied with temporary disorientation, often associated with physical in-coordination. Sleep inertia often lasts 30-120 minutes after waking in the morning. Sleep inertia may be the most common after oversleeping, after daytime naps if stages 3 and 4 of NREM sleep are entered, which is usual if a nap lasts for more than 30 minutes. Intrusion of wakefulness after REM sleep may be responsible for sleep paralysis at the end of a period of sleep. Awareness of the environment is accompanied by the motor inhibition of REM sleep.

Older people frequently experience insomnia due to age-related changes in sleep. The sleep cycle in this population is characterized by lighter sleep, more frequent awakenings, and less total sleep time. In fact, the relative amount of REM sleep generally decreases with age. Research has shown that the negative effects of poor sleep quality include reduced cognitive ability, a greater propensity for falls, low energy levels, potential for dizziness, drowsiness, etc. In fact, falling is a major cause of injury and mortality in elderly people.

DETAILED DESCRIPTION

Figure 1:
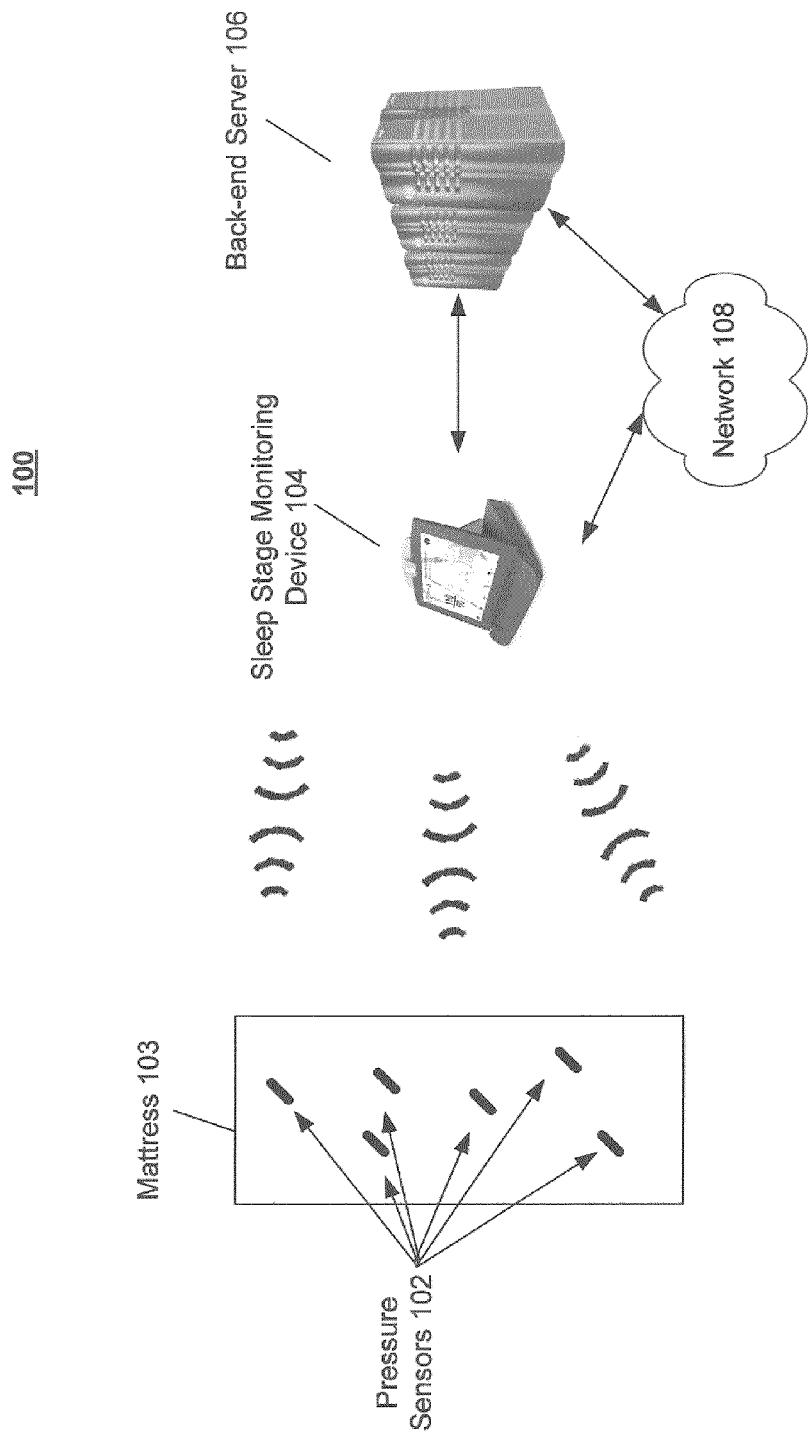
FIG. 1 illustrates one embodiment of a system.

Various embodiments of the present invention may be generally directed to monitoring sleep stages to determine optimal arousal times and to alert an individual to negative states of wakefulness. As described above, getting adequate deep sleep (stages 3 and 4 of NREM sleep) and REM sleep should be encouraged. Intrusion of wakefulness from stages 3 and 4 of NREM sleep and REM sleep may have negative consequences such as drowsiness, a feeling of not being refreshed, bad moods, experiences of "disorders of arousal", and so forth. The commonest and mildest example of "disorders of arousal" is sleep inertia. As described above, sleep inertia is often accompanied with temporary disorientation and is often associated with physical in-coordination. Thus, when one experiences sleep inertia the chances of an injury occurring due to a fall, for example, increases. This is particularly true for the elderly in general. In fact, sleep inertia or just increased intrusion of wakefulness from stages 3 and 4 of NREM and REM sleep may increase when an individual resides in a healthcare facility or long term stay institution. Here, irregular sleeping patterns or negative states of wakefulness may be common due to strangeness of the environment, increased activity due to medication administration and staff rounds, varying lighting conditions, roommates, and so forth.

Embodiments of the invention monitor sleep stages of an individual via one or more pressure sensors located under the mattress of the individual. Based on the current sleep stage of the individual, embodiments of the invention provide for optimal arousal time indicators to inform another person of the best time to wake the individual. Knowing the optimal arousal times to wake the individual may be particularly useful to staff members of a healthcare facility or long term stay institution, for example. In embodiments, optimal arousal times include when the individual is in stages 1 or 2 of NREM sleep. For example, nurses, doctors and visitors may use the optimal arousal time indicators to not alert the individual when in deep sleep (stages 3 and 4 of NREM sleep) and REM sleep due to the negative consequences of arousal from these sleep stages. Waking the individual during optimal arousal times helps to ensure adequate sleep quality, which is essential for recovery and recuperation. In addition, waking the individual during optimal arousal times may help to reduce sleep inertia and thus help to reduce the risk of falls or personal injuries to the individual.

Too much daytime napping may negatively affect nighttime sleep. Embodiments of the invention monitor when an individual is experiencing excessive daytime sleep and attempts to awaken the individual during optimal arousal times using sensory alertness techniques.

As mentioned above, embodiments of the invention monitor sleep stages of an individual. When the individual is awakened during non-optimal times (e.g., stages 3 and 4 of NREM sleep and REM sleep) or has not experienced quality sleep, the individual may experience negative states of wakefulness. During negative states of wakefulness, the individual may be at risk if he or she attempts to perform certain tasks like walking up or down stairs, operating the stove or oven, driving a car, and so forth. Embodiments of the invention alert the individual to the negative states of wakefulness by activating a normally dormant sensor network in the individual's environment that warns the individual that he or she may be at risk of falling or have temporarily reduced cognitive capacity. Other embodiments may be described and claimed.

Various embodiments may comprise one or more elements or components. An element may comprise any structure arranged to perform certain operations. Each element may be implemented as hardware, software, or any combination thereof, as desired for a given set of design parameters or performance constraints. Although an embodiment may be described with a limited number of elements in a certain topology by way of example, the embodiment may include more or less elements in alternate topologies as desired for a given implementation. It is worthy to note that any reference to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

FIG. 1 illustrates one embodiment of a system 100 for monitoring sleep stages to generate optimal arousal time indicators. In one embodiment, system 100 comprises one or more pressure sensors 102 positioned under a mattress 103, a sleep stage monitoring device 104, a back-end server 106 and a network 108. Each of these components is described next in more detail.

In embodiments, pressure sensors 102 are incorporated into or associated with furniture in which an individual may use for sleeping. In FIG. 1, pressure sensors 102 are illustrated as being incorporated into or placed under mattress 103, but embodiments of the invention are not limited to this. In fact, pressure sensors 102 may be incorporated into or associated with any piece of furniture, including but not limited to a chair, sofa, and so forth. Pressure sensors 102 may be placed under or incorporated into a matt or rug, for example, if the individual tends to sleep on the floor.

In embodiments, the trigger point for each pressure sensor 102 may be adjusted according to the size and/or weight of the furniture to which it is incorporated, associated or attached. The adjustment of the trigger point may be needed because using a heavier piece of furniture for sleeping generally results in a lighter shock or pressure to that piece of furniture than it would to a lighter piece of furniture. In addition, the adjustments of the trigger point may be needed due to the thickness of a mattress or the size/weight of the individual.

In embodiments, each time pressure is detected by one of sensors 102, the pressure data is sent to monitoring device 104. One or more of pressure sensors 102 may be connected directly to monitoring device 104. Here, an A/D conversion of the pressure data may be accomplished via an A/D converter in device 104. The collected pressure data may also be wirelessly transmitted to device 104 via, for example, Bluetooth technology, Zigbee technology or a proprietary system. In an embodiment, the A/D conversion of the collected data may be accomplished via an A/D converter in the sensor itself. In an embodiment, the converted data may be transferred via a radio in the sensor to a radio in device 104. The invention is not limited to these example wireless technologies/examples. Alternatively, sensors 102 may transmit data to device 104 via some combination of wireless and wired connection technologies.

Sleep stage monitoring device 104 receives the pressure data from pressure sensors 102. In embodiments, device 104 then uses the data to determine NREM and REM sleep stages for the individual through physiological patterns, as will be described in more detail below with reference to FIGS. 2-5. Based on the current sleep stage of the individual, embodiments of the invention provide for optimal arousal time indicators to inform another person of the best time to wake the individual. In embodiments, optimal arousal times include when the individual is in stages 1 or 2 of NREM sleep. Knowing the optimal arousal times to wake the individual may be particularly useful to staff members of a healthcare facility or long term stay institution, for example. As mentioned above, nurses, doctors and visitors may use the optimal arousal time indicators to not wake the individual when in deep sleep (stages 3 and 4 of NREM sleep) and REM sleep due to the negative consequences of arousal from these sleep stages. Waking the individual during optimal arousal times helps to ensure adequate sleep quality, which is essential for recovery and recuperation. In addition, waking the individual during optimal arousal times may help to reduce sleep inertia and thus help to reduce the risk of falls or personal injuries to the individual.

In embodiments, device 104 may transmit all of the data related to the individual to back-end server 106 for further analysis by the individual's physician, for example. The data may be transmitted via network 108 (e.g., the Internet, a local area network (LAN), a wide area network (WAN), etc.) or via a direct connection between device 104 and back-end server 106 or a connection that involves a combination of wireless and wired technologies.

In one embodiment, sleep stage monitoring device 104 may be any device capable of performing the functionality of the invention described herein. Device 104 may be implemented as part of a wired communication system, a wireless communication system, or a combination of both. In one embodiment, for example, device 104 may be implemented as a mobile computing device having wireless capabilities. A mobile computing device may refer to any device having a processing system and a mobile power source or supply, such as one or more batteries, for example.

Examples of embodiments of a mobile computing device that may be adapted to include the functionality of the present invention include a laptop computer, ultra-laptop computer, portable computer, handheld computer, palmtop computer, personal digital assistant (PDA), cellular telephone, combination cellular telephone/PDA, smart phone, pager, one-way pager, two-way pager, messaging device, data communication device, and so forth.

Examples of such a mobile computing device also may include computers that are arranged to be worn by a person, such as a wrist computer, finger computer, ring computer, eyeglass computer, belt-clip computer, arm-band computer, shoe computers, clothing computers, and other wearable computers.

In various embodiments, system 100 may be implemented as a wireless system, a wired system, or a combination of both. When implemented as a wireless system, system 100 may include components and interfaces suitable for communicating over a wireless shared media, such as one or more antennas, transmitters, receivers, transceivers, amplifiers, filters, control logic, and so forth. An example of wireless shared media may include portions of a wireless spectrum, such as the RF spectrum and so forth. When implemented as a wired system, system 100 may include components and interfaces suitable for communicating over wired communications media, such as input/output (I/O) adapters, physical connectors to connect the I/O adapter with a corresponding wired communications medium, a network interface card (NIC), disc controller, video controller, audio controller, and so forth. Examples of wired communications media may include a wire, cable, metal leads, printed circuit board (PCB), backplane, switch fabric, semiconductor material, twisted-pair wire, co-axial cable, fiber optics, and so forth.

Operations for the above embodiments may be further described with reference to the following figures and accompanying examples. Some of the figures may include a logic flow. Although such figures presented herein may include a particular logic flow, it can be appreciated that the logic flow merely provides an example of how the general functionality as described herein can be implemented. Further, the given logic flow does not necessarily have to be executed in the order presented unless otherwise indicated. In addition, the given logic flow may be implemented by a hardware element, a software element executed by a processor, or any combination thereof.

Figure 2:
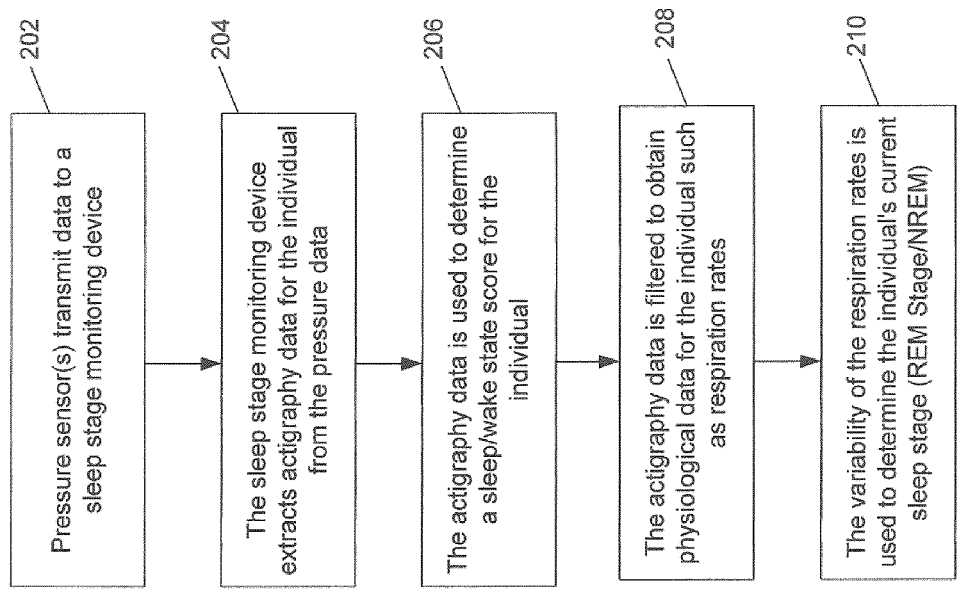
FIG. 2 illustrates one embodiment of a logic flow.

FIG. 2 illustrates one embodiment of a logic flow 200. The logic flow 200 may be representative of the operations executed by one or more embodiments described herein, for example, the operations executed by system 100.

Referring to FIG. 2, pressure sensors (such as sensors 102 from FIG. 1) collect pressure data for an individual and transmit the data to a device (such as sleep stage monitoring device 104 from FIG. 1) (block 202). The sleep stage monitoring device receives the data from the pressure sensors and extracts actigraphy or movement data for the individual from the pressure data via well known methods (block 204). The actigraphy data is used to determine a sleep/wake state score for the individual via well known methods (block 206). Here, it is determined whether the individual is sleeping or awake.

Figure 3:
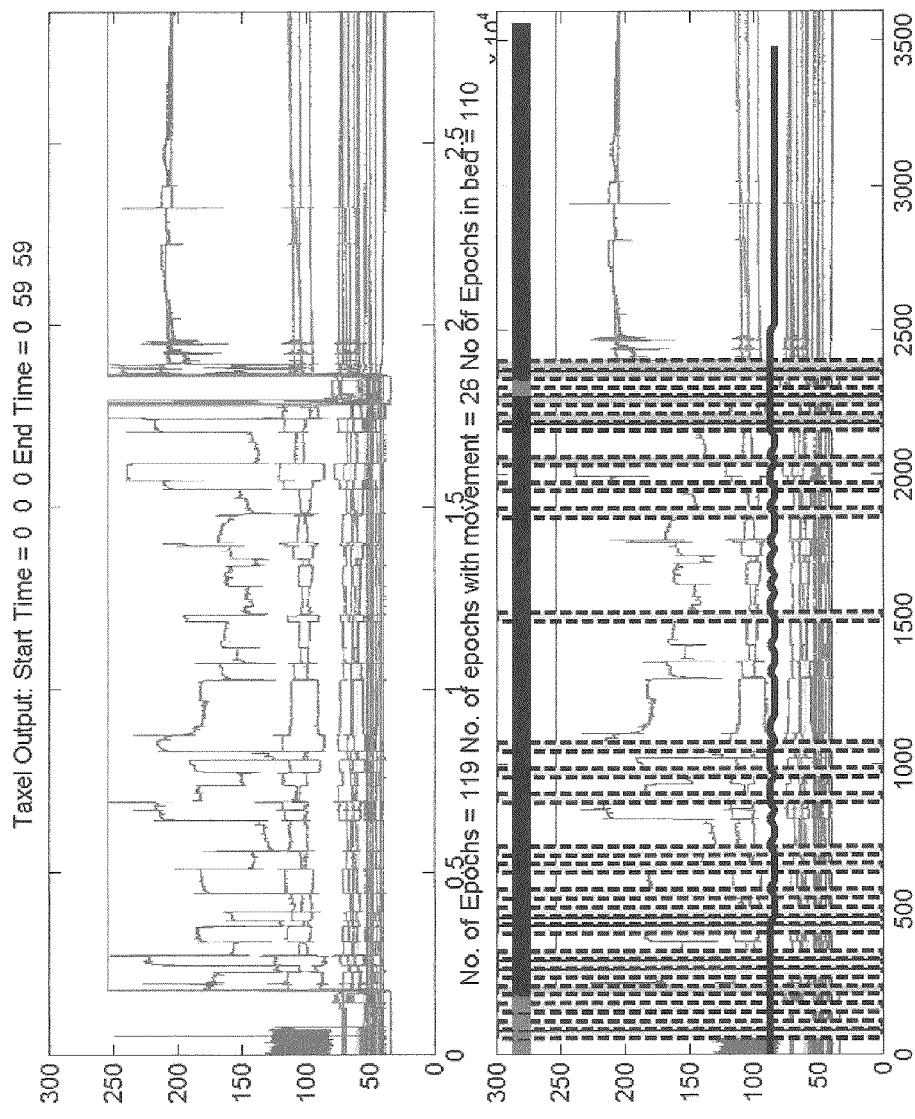
FIG. 3 illustrates example actigraphy data extracted from data obtained from pressure sensors(s)

FIG. 3 illustrates an actigraphy extraction from an hour period of sleep of an elderly individual. Referring to FIG. 3, the top chart represents 1 hour of data from a pressure sensing device that has 24 individual sensors incorporated. The data is examined in 30 second windows to measure actigraphy. Regarding the bottom chart, within a single 30 second window if the variation of data of an individual sensor exceeds a certain threshold, that 30 second window is considered an epoch of movement and is used to increment actigraphy and thus sleep/wake measurements. The vertical columns in the bottom chart are used to represent epochs of movements. Data that is not considered movement is further analyzed to extract respiration data to make distinctions between REM and NREM sleep. FIG. 3 is provided for illustration purposes only and is not meant to limit embodiments of the invention.

Referring back to FIG. 1, if asleep, the device filters the actigraphy data to obtain physiological data for the individual such as respiration rates via well known methods (block 208). The device uses the variability of the respiration rates to determine the individual's current sleep stage (block 210). In embodiments, the sleep stages may include stages 1-4 of NREM sleep and REM sleep.

Figure 4:
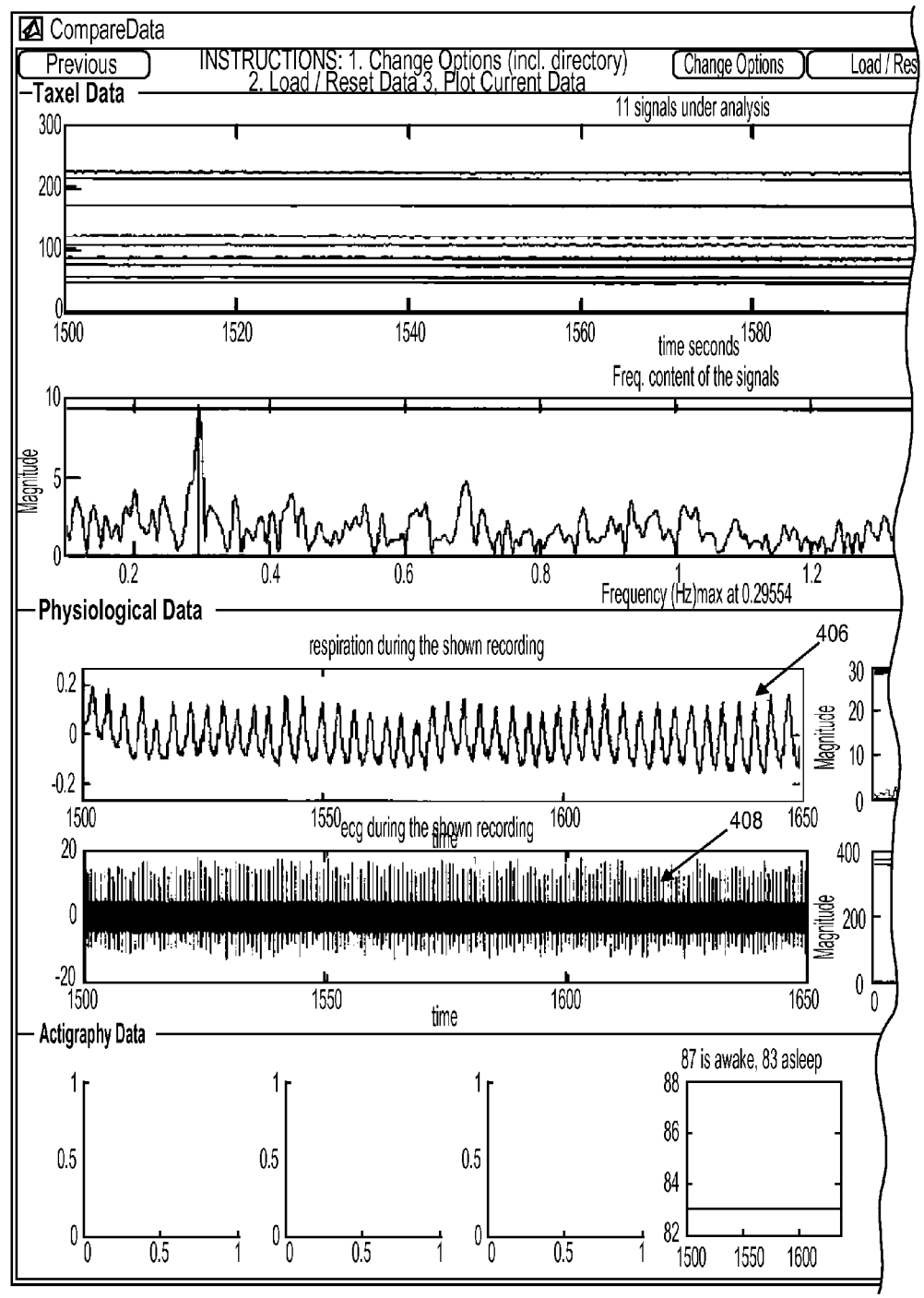
FIG. 4 illustrates example respiration data extracted from data obtained from pressure sensor(s).
Figure 4:
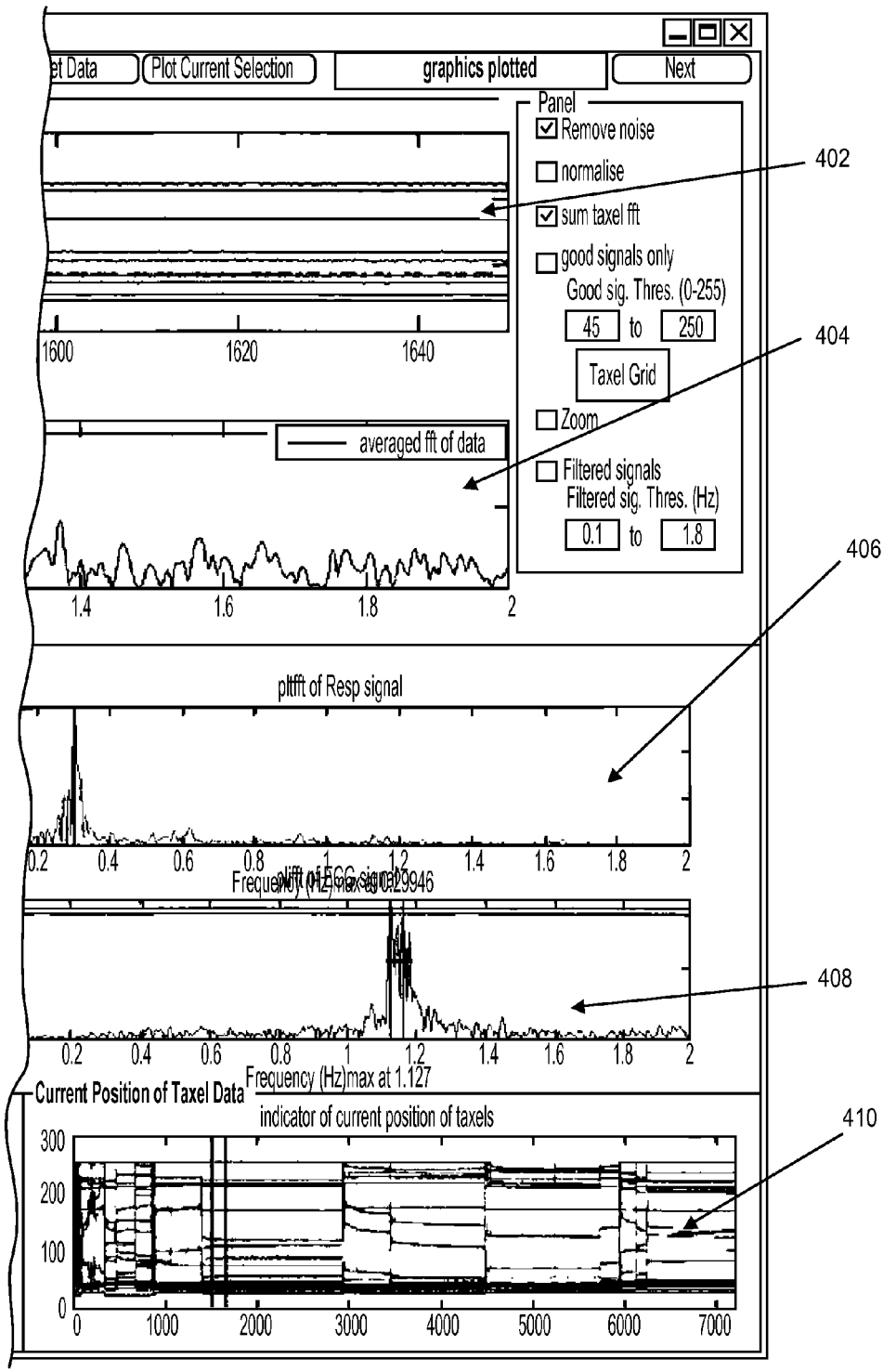

FIG. 4 illustrates a respiration rate measured from a pressure sensor=0.2955 Hz and with a respiration rate measured from PSG=0.29946 Hz. Referring to FIG. 4, the chart as indicated by arrow 402 illustrates a 30 second window showing data from 24 individual pressure sensors. The chart as indicated by arrow 404 illustrates a frequency analysis window showing FFT of pressure sensor data. The extracted frequency (signal peak) was measured to be 0.29954 Hz, which corresponds to the respiration rate. The charts as indicated by arrows 406 illustrate respiration data and frequency analysis taken from simultaneously recorded PSG data. Corresponding PSG respiration data was recorded to be 0.29946 Hz from the same 30 second window as the pressure data. The charts as indicated by arrows 408 illustrate ECG data and frequency analysis taken from simultaneously recorded PSG data. The chart as indicated by arrow 410 illustrates complete data showing 30 second window under analysis. FIG. 4 is provided for illustration purposes only and is not meant to limit embodiments of the invention.

As mentioned above, based on the current sleep stage of the individual, embodiments of the invention provide for optimal arousal time indicators to information another person of the best time to wake the individual. An embodiment of this is illustrated in a logic flow 500 of FIG. 5. The logic flow 500 may be representative of the operations executed by one or more embodiments described herein, for example, the operations executed by system 100.

Figure 5:
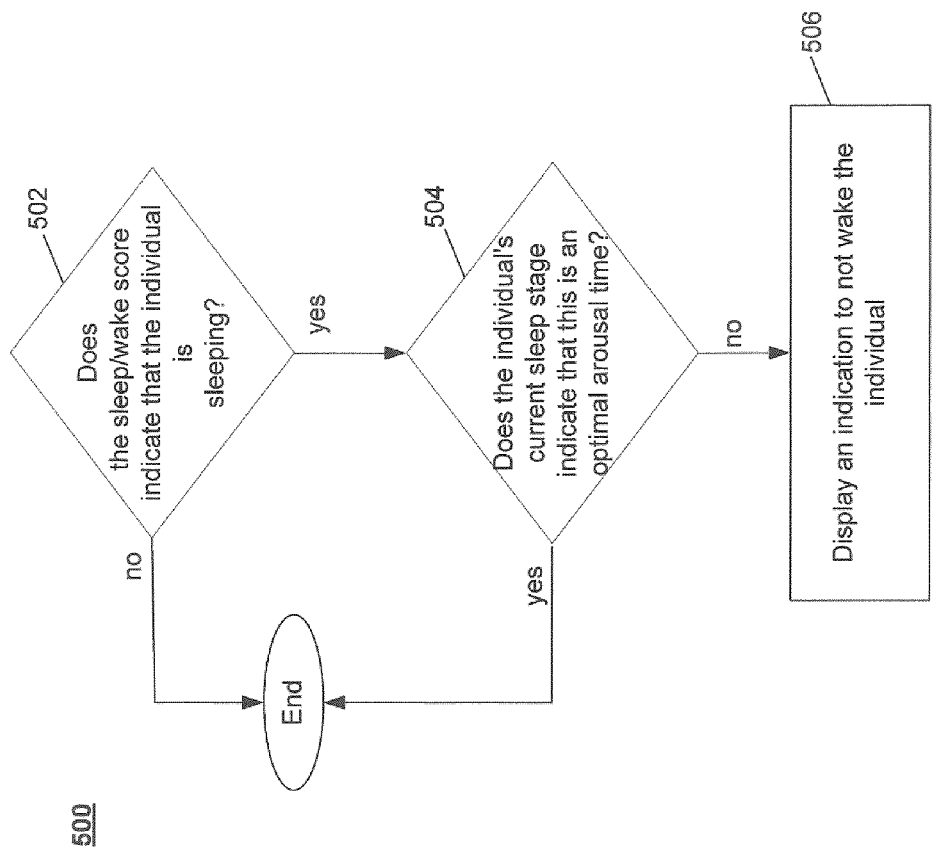
FIG. 5 illustrates one embodiment of a logic flow.

Referring to FIG. 5, it is determined whether the sleep/wake state score derived from the actigraphy data indicates that the individual is sleeping (block 502). If so, then it is determined whether the individual's current sleep stage indicates that this is an optimal arousal time (block 504). In embodiments, optimal arousal times include when the individual is in stages 1 or 2 of NREM sleep. Waking the individual during optimal arousal times helps to ensure sufficient sleep quality and may help to reduce sleep inertia and thus help to reduce the risk of falls or personal injuries. If not an optimal arousal time for the individual, then the sleep stage monitoring device causes the display of an indication to not wake the individual (block 506). Alternatively, in embodiments, the monitoring device may cause the display of an indication to wake the individual when the individual's current sleep stage indicates that this is an optimal arousal time for the individual.

As mentioned above, too much daytime napping may negatively affect nighttime sleep. In embodiments, the sleep stage monitoring device (such as sleep stage monitoring device 104 of FIG. 1) may be adapted to monitor when an individual is experiencing excessive day time sleep and attempt to awaken the individual during optimal arousal times using sensory alertness techniques. An embodiment of this is illustrated in a logic flow 600 of FIG. 6. The logic flow 600 may be representative of the operations executed by one or more embodiments described herein, for example, the operations executed by system 100.

Figure 6:
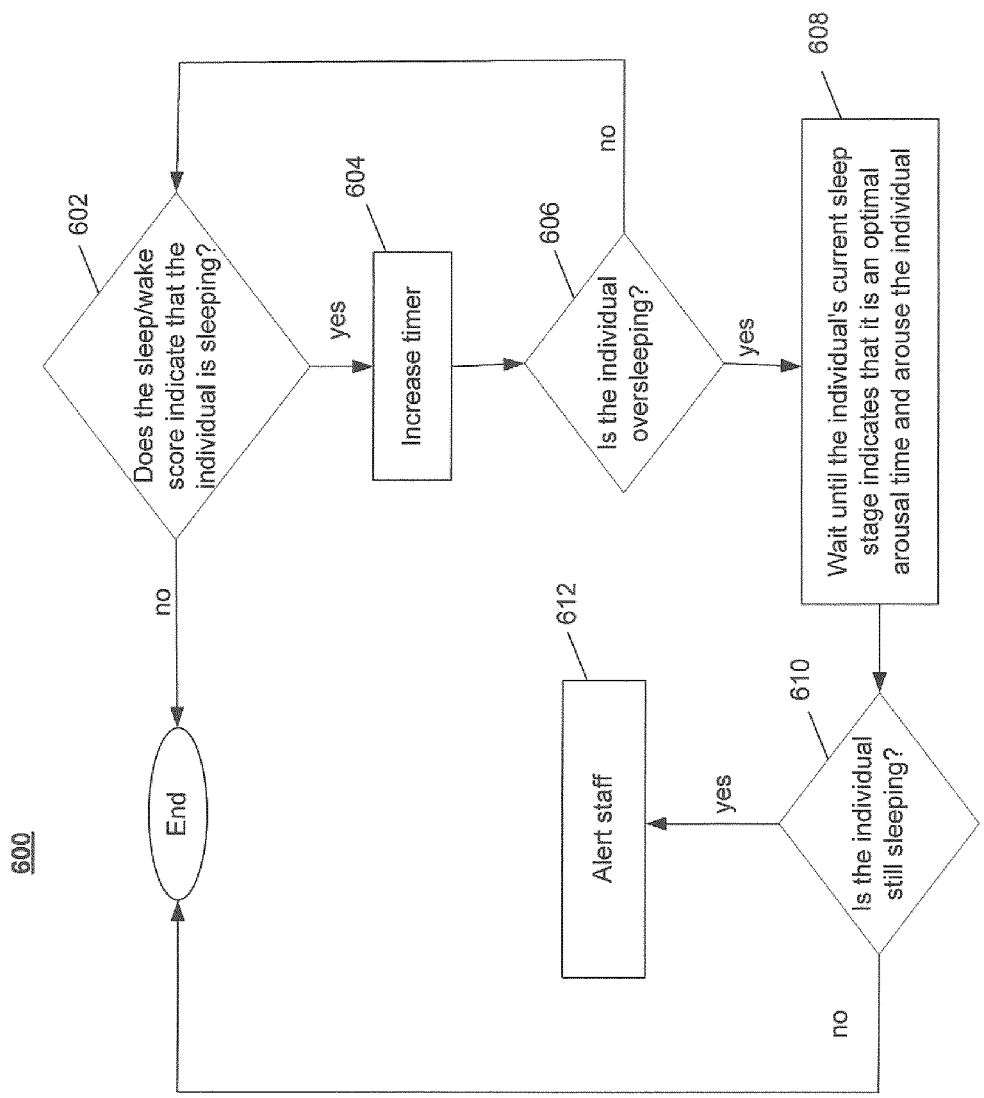
FIG. 6 illustrates one embodiment of a logic flow.

Referring to FIG. 6, while an individual's sleep/wake score indicates that the individual is sleeping (block 602), then a timer is increased (block 604). It is determined whether the individual is oversleeping (block 606). If so, the sleep stage monitoring device waits until the individual's current sleep stage indicates that it is an optimal arousal time for the individual (as described above) and arouses the individual using a sensory alertness technique (block 608).

In embodiments, various sensory alertness techniques may be used to arouse the individual. For example, sensory alertness techniques may include audio, such as music, that starts out softer and eventually becomes louder. Another possible example of sensory alertness techniques may include vibrating the furniture (e.g., chair, bed, and so forth) on which the individual is sleeping to arouse the individual. In embodiments, if one type of sensory alertness technique is not waking the individual, then another technique may be used.

If the individual fails to awaken (block 610), then staff may be alerted (block 612). The example sensory alertness techniques provided herein are for illustration purposes only and are not meant to limit embodiments of the invention. Embodiments contemplate using any sensory alertness technique that complements the goals of the invention. For example, a goal of embodiments of the invention is to ensure that the individual is able to awake in a non-abrupt or disorienting fashion in the correct stage of sleep (e.g., during an optimal arousal time) prior to the day's events such as meal times, medication, trips, and so forth.

As mentioned above, embodiments of the invention monitor sleep stages of an individual. When the individual is awakened during non-optimal times (e.g., stages 3 and 4 of NREM sleep and REM sleep) or has not experienced quality sleep, the individual may experience negative states of wakefulness. During negative states of wakefulness, the individual may be at risk if he or she attempts to perform certain tasks like walking up or down stairs, driving a car, operating the stove or oven or fireplace, and so forth. Embodiments of the invention alert the individual to the negative states of wakefulness by activating a normally dormant sensor network in the individual's environment that warns the individual that he or she may be at risk of falling or have temporarily reduced cognitive capacity.

Figure 7:
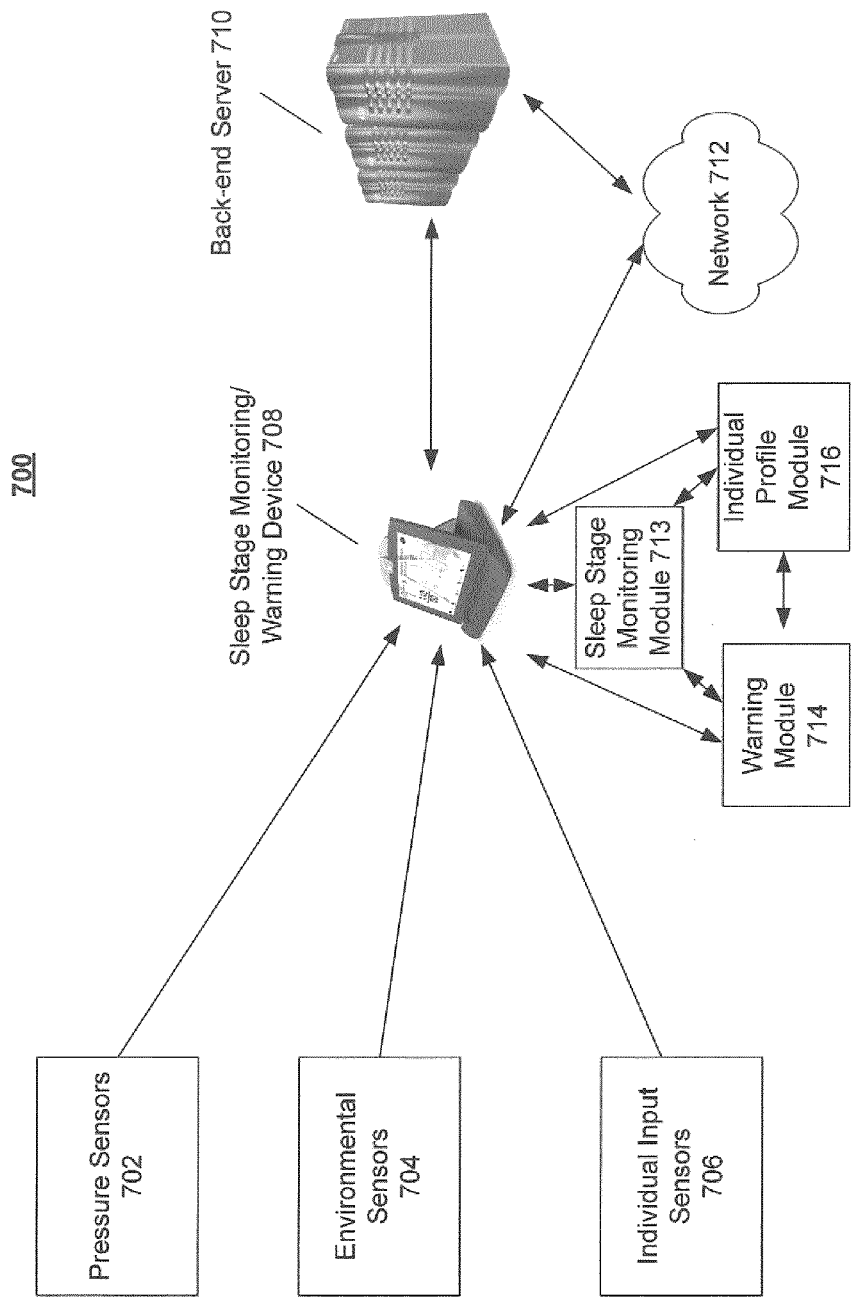
FIG. 7 illustrates one embodiment of a system.

An embodiment of a system 700 for alerting an individual to a potentially dangerous situation while experiencing negative states of wakefulness is illustrated in FIG. 7. In one embodiment, system 700 comprises one or more pressure sensors 702, one or more environmental sensors 704, one or more individual input sensors 706, a sleep stage monitoring/warning device 708, a back-end server 710 and a network 712. In embodiments, device 708 may access one or more of a sleep stage monitoring module 713, a warning module 714 and an individual profile module 716. Each of these components is described next in more detail.

In one embodiment, sleep stage monitoring/warning device 708 may include all of the functionally of sleep stage monitoring device 104 as described above with reference to FIG. 1 (via, for example, sleep stage monitoring module 713). Here, device 708 may be further adapted to include the warning functionality as described herein (via, for example, warning module 714 and individual profile module 716). Some of modules 713, 714 and 716 may be directly integrated into device 708 or may be coupled to device 708 via a connection (e.g., wireless, wired or some combination of both). Note that although the functionality of modules 713, 714 and 716 is described herein as being separated into three components, this is not meant to limit the invention. In fact, this functionality may be combined into one or two components, or separated into four or more components. Additionally, modules 713, 714 and 716 may be customized for an individual. As described above with reference to system 100 of FIG. 1, in various embodiments, system 700 may be implemented as a wireless system, a wired system, or a combination of both.

At a high level and in an embodiment, real-time data may be collected for an individual via pressure sensors 702, environmental sensors 704 and/or individual input sensors 706. The collected data are transmitted to sleep stage monitoring/warning device 708. Device 708 processes the data to determine whether the individual is awakened during non-optimal times (e.g., stages 3 and 4 of NREM sleep and REM sleep) or has not experienced quality sleep (as was described above). In this situation, the individual may be experiencing negative states of wakefulness. If so, then device 708 may alert a normally dormant sensor network in the individual's environment that the individual may be placing his or herself in a potentially dangerous situation due to a temporarily reduced cognitive capacity. If a potentially dangerous situation is detected, then device 708 determines an appropriate warning to administer to the individual (via, for example, warning module 714 and individual profile module 716). The warning is administered via a normally dormant sensor network in the individual's environment.

Embodiments of the invention provide for many types of possible warnings including, but not limited to, an warning such as a light flashing or audible alarm beeping when the individual approaches the potentially dangerous condition. A potentially dangerous condition may include, but not limited to, approaching a stairwell, a motor vehicle, a gas stove or oven, or an area where medication is kept, and so forth. These example warnings/potentially dangerous conditions are provided for illustration purposes only and are not meant to limit the invention.

As discussed above, real-time data may be continuously collected for an individual via pressure sensors 702, environmental sensors 704 and/or individual input sensors 706. The collected data may be wirelessly transmitted to sleep stage monitoring/warning device 708 via, for example, Bluetooth technology, Zigbee technology or a proprietary system. The invention is not limited to these example wireless technologies. Alternatively, sensors 702, 704 and/or 706 may transmit data to device 708 via a wired connection, or some combination of wireless and wired connection technologies.

Sensors 702, 704 and/or 706 may also be adapted to store real-time data via integrated long term storage, such as flash memory for example, and then transmit the data to sleep stage monitoring/warning device 708 at a later time. The integrated long term storage helps to ensure that no collected data are lost if the connection to device 708 is currently not available.

In embodiments, pressure sensors 702 may be similar to what was described above with reference to FIG. 1. In embodiments, environmental sensors 704 may include any means of monitoring the individual's environment. For example, sensors 704 may include location sensors in the individual's home to detect where the individual is within the home and to help monitor the individual at home. Such location sensors may be placed in different rooms in the home and may interact with identification sensors that are worn and/or incorporated into sleep stage monitoring/warning device 708, and so forth. For example, location sensors may help device 708 to determine that the individual is approaching a potentially dangerous area in the home, such as stairs.

Environmental sensors 704 may also include door switches within the home that detect when doors are opened. Door switches may help device 708 to determine which room the individual has just entered. A door switch may be, for example, a magnetic reed switch, or may be a sensor that detects that the door has moved. Environmental sensors 704 are not limited to these examples.

In embodiments of the invention, individual input sensors 706 may include various ways in which an individual may provide data or feedback to sleep stage monitoring/warning device 708 via direct or indirect input into device 708. This may include, but is not necessarily limited to, health data such as the age of the individual, physical limitations of the individual that may worsen the symptoms of sleep inertia, for example, and so forth. The data provided to device 708 via individual input sensors 706 may be stored in individual profile module 716, for example. Physical limitations of the individual may also assist device 708 (or dangerous situation module 714) to determine an appropriate warning to administer to the individual. For example, if the individual provides information to device 708 that states the individual is blind, then device 708 will not administer a visual warning to the individual.

Embodiments of the invention may use data (e.g., sleep stage data, environmental data and individual data) to determine when an individual may be potentially in danger. Here, device 708 (via module 714) may process data stored in sleep stage monitoring module 713 and/or individual profile module 716 to warn the user of the potentially dangerous situation by activating or alerting a normally dormant sensor system in the individual's environment. Here, in embodiments, a user may be prompted to not perform certain activities while experiencing sleep inertia or poor quality of sleep (e.g., negative states of wakefulness). For example, a person who has very dilated eyes (known from past medical records stored in individual profile module 716) would be prompted to not move around the house while experiencing sleep inertia, and so forth.

In embodiments, device 708 may transmit all of the data related to the individual to back-end server 710 for further analysis by the individual's physician, for example. The data may be transmitted via network 712 (e.g., the Internet, a local area network (LAN), a wide area network (WAN), etc.) or via a direct connection between device 708 and back-end server 710 or a connection that involves a combination of wireless and wired technologies.

Figure 8:
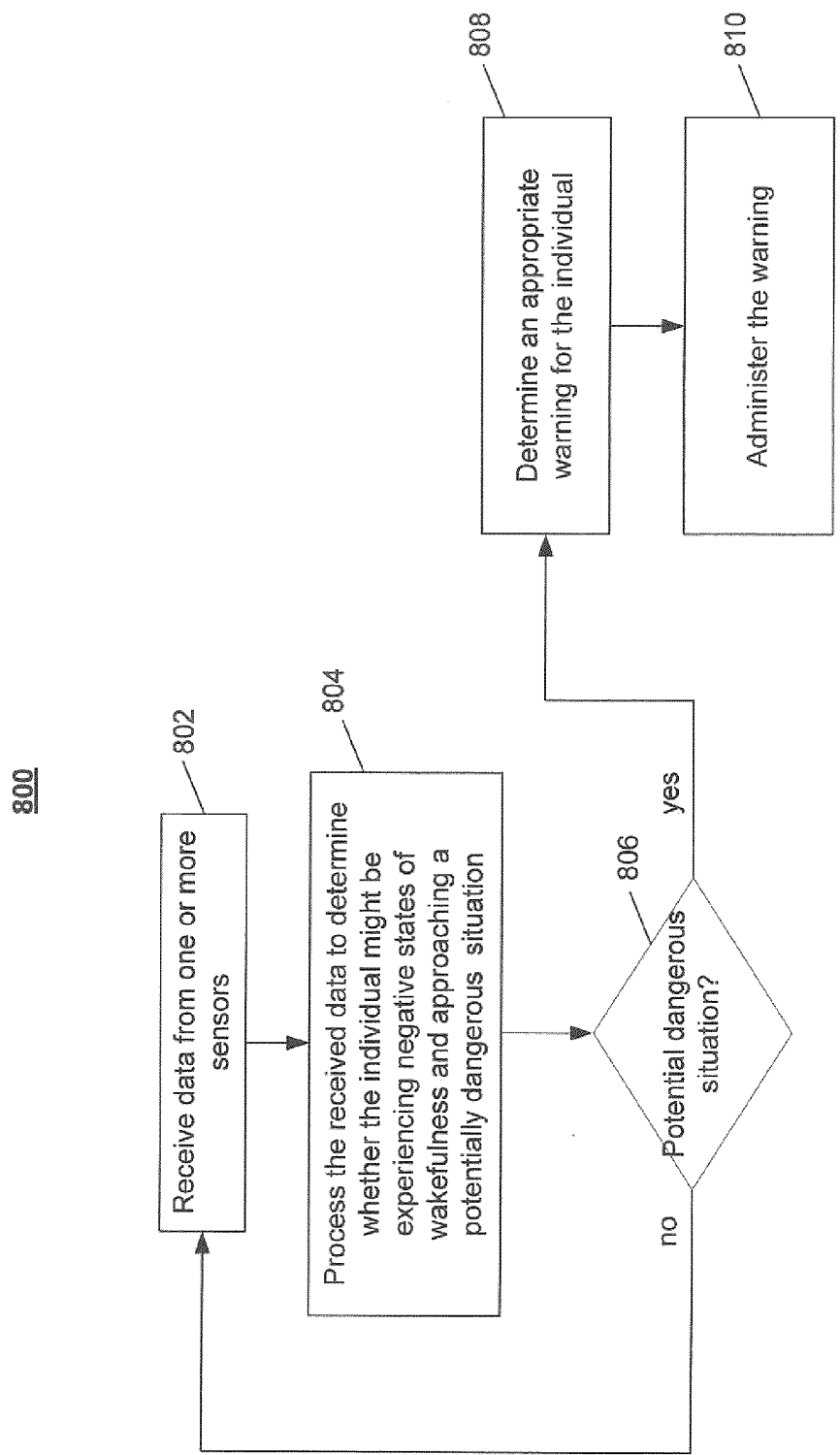
FIG. 8 illustrates one embodiment of a logic flow.

FIG. 8 illustrates one embodiment of a logic flow 800. Each of the blocks in logic flow 800 was described in more detail above. As shown in logic flow 800, a device (such as sleep stage monitoring/warning device 708 from FIG. 7) receives data from one or more sensors (such as sensors 702, 704 and/or 706 from FIG. 7) (block 802). The device processes the received data to determine whether the individual might be experiencing negative states of wakefulness when waking from sleep and approaching a potentially dangerous situation (block 804). In embodiments, a negative state of wakefulness is when the individual wakes from either stages 3 or 4 of non-rapid eye movement (NREM) sleep or the REM sleep stage. If so, then the device processes the data to determine a warning for the individual (block 808). The device then administers the warning to the individual (block 810).

Figure 9:
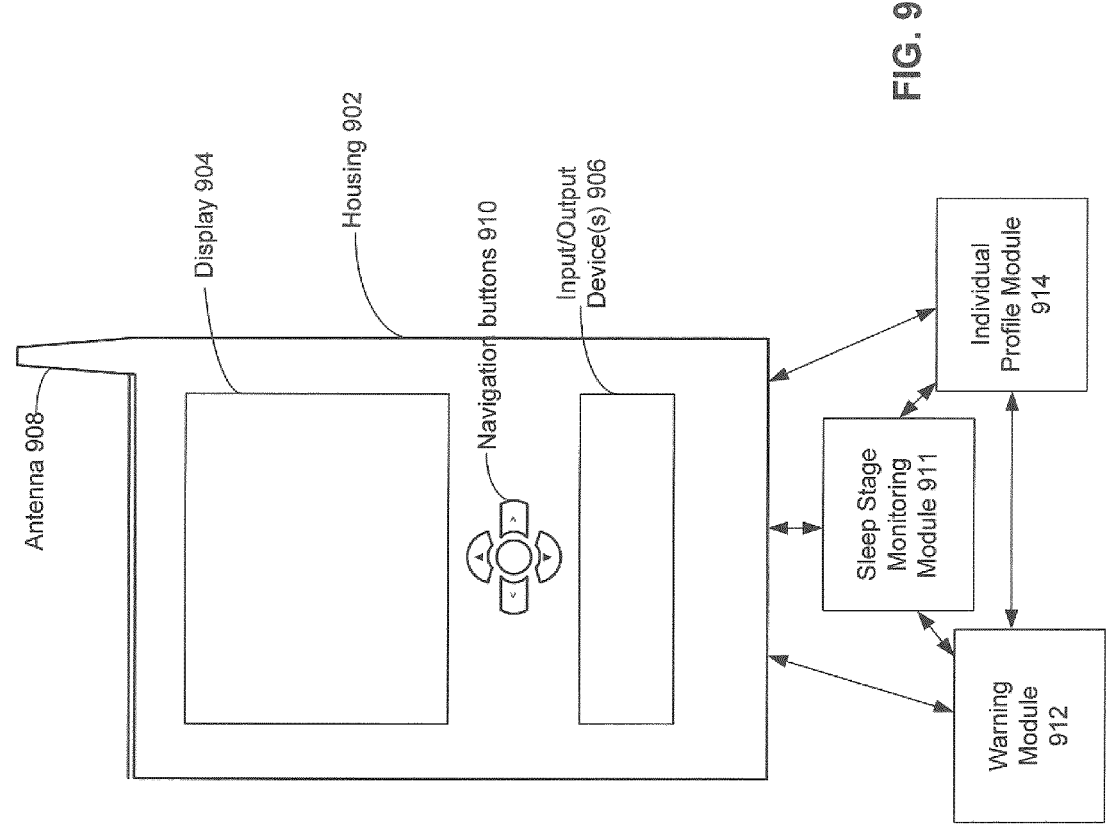
FIG. 9 illustrates one embodiment of a device.

FIG. 9 illustrates one embodiment of a device 900 in which functionality of the present invention as described herein may be implemented (e.g., sleep stage monitoring device 104 from FIG. 1 or sleep stage monitoring/warning device 708 from FIG. 7). Referring to FIG. 9, device 900 may include a housing 902, a display 904, one or more input/output devices 906, an antenna 908, navigation buttons 910, a sleep stage monitoring module 911, a warning module 912 and an individual profile module 914.

Some of modules 911, 912 and 914 may be directly integrated into device 900 or may be coupled to device 900 via a connection (e.g., wireless, wired or some combination of both). Note that although the functionality of modules 911, 912 and 914 is described herein as being separated into three components, this is not meant to limit the invention. In fact, this functionality may be combined into one or two components, or separated into four or more components. Additionally, modules 911, 912 and 914 may be customized for an individual. Each of the components of FIG. 9 is described next in more detail.

Housing 902 may comprise any suitable housing, but typically involves a small form factor to enable device 900 to be easily transportable.

Display 904 may comprise any suitable display unit for displaying information appropriate for a mobile computing device. Display 904 is used by the invention to display warnings to the individual, to assist with input into device 900, and so forth.

I/O device(s) 906 may comprise any suitable I/O device for entering information into and receiving information from device 900. Examples for I/O device(s) 906 may include touch screen interfaces, simple menus with icon selection, gestural manipulation of the device, a suitable alphanumeric keyboard, a numeric keypad, a touch pad, input keys, buttons, switches, rocker switches, a microphone, a speaker, voice recognition device and software, as well as all of the sensing described above, and so forth. Information may be entered into device 900 by way of microphone. Such information may be digitized by a voice recognition device. The embodiments are not limited in this context.

Antenna 908 is used to facilitate wireless communication with device 900.

In one embodiment, navigation buttons 910 comprise an upward navigation button, a downward navigation button, a leftward navigation button, and a rightward navigation button. Navigation buttons 910 also may comprise a select button to execute a particular function on device 900.

In embodiments, sleep stage monitoring module 911, warning module 912 and individual profile module 914 are adapted to include the functionality of embodiments of the invention as described herein.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Some embodiments may be implemented, for example, using a machine-readable or computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

Numerous specific details have been set forth herein to provide a thorough understanding of the embodiments. It will be understood by those skilled in the art, however, that the embodiments may be practiced without these specific details. In other instances, well-known operations, components and circuits have not been described in detail so as not to obscure the embodiments. It can be appreciated that the specific structural and functional details disclosed herein may be representative and do not necessarily limit the scope of the embodiments.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A system, comprising:
a device adapted to receive pressure data from at least one pressure sensor, wherein the at least one pressure sensor is associated with furniture used for an individual to sleep, wherein the device is adapted to use the pressure data to determine a sleep stage for the individual, wherein the sleep stage is to be used to determine whether it is an optimal arousal time for the individual, and wherein the device is adapted to output an indication to not wake the individual if it is not the optimal arousal time for the individual, and wherein the device is adapted to set an adjustable trigger point of the at least one pressure sensor based on the individual's weight, the sensor's location on or in the furniture, or any combination thereof.

2. The system of claim 1, wherein the optimal arousal time for the individual is when the sleep stage is either stage 1 or stage 2 of non-rapid eye movement (NREM) sleep.

3. The system of claim 1, further comprising the furniture associated with the at least one pressure sensor, wherein the furniture is a matt or rug.

4. The system of claim 1, wherein the device is adapted to use the pressure data to determine a sleep stage by extracting actigraphy data from the pressure data and filtering the actigraphy data to obtain respiration rates, wherein the respiration rates are used to determine the sleep stage.

5. The system of claim 1, wherein the device is adapted to monitor the individual to determine oversleeping and wherein the device is adapted to attempt to arouse the individual during the optimal arousal time when the individual is oversleeping.

6. The system of claim 1, wherein the device is adapted to set the adjustable trigger point of the at least one pressure sensor based on the individual's weight.

7. The system of claim 1, wherein the device is adapted to set the adjustable trigger point of the at least one pressure sensor based on the sensor's location on or in the furniture.

8. A system, comprising:
an environmental sensor adapted to monitor an individual's environment;
a device adapted to receive pressure data from at least one pressure sensor, wherein the at least one pressure sensor is associated with furniture used for the individual to sleep, wherein the device is adapted to set an adjustable trigger point of the at least one pressure sensor based on the individual's weight, the sensor's location on or in the furniture, or any combination thereof, wherein the device is adapted to use the pressure data to determine a sleep stage for the individual, wherein the sleep stage is to be used to determine whether the individual is in a negative state of wakefulness when the individual wakes from sleep.

9. The system of claim 8, wherein the negative state of wakefulness is when the individual wakes from one of stages 3 and 4 of non-rapid eye movement (NREM) sleep and REM sleep stage.

10. The system of claim 8, further comprising the furniture associated with the at least one pressure sensor, wherein the furniture is a matt or rug.

11. The system of claim 8, wherein the using the pressure data to determine a sleep stage includes extracting actigraphy data from the pressure data and filtering the actigraphy data to obtain respiration rates, wherein the respiration rates are used to determine the sleep stage.

12. The system of claim 8, wherein the environmental sensor is a door switch sensor.

13. The system of claim 8, wherein the device is adapted to cause a warning to the individual when the individual is in a negative state of wakefulness and is approaching a dangerous situation.

14. The system of claim 13, wherein the device is adapted to detect the dangerous situation through receiving data relating to the individual's environment from the environmental sensor, wherein the individual's environment comprises one or more rooms.

15. The system of claim 14, wherein the environmental sensor is configured to detect the individual entering one of the one or more rooms.

16. A method, comprising:
setting an adjustable trigger point of at least one pressure sensor associated with furniture used for an individual to sleep, the trigger point based on the individual's weight, the sensor's location on or in the furniture, or any combination thereof;

receiving pressure data from the at least one pressure sensor;

using the pressure data to determine a sleep stage for the individual;

determining whether the sleep stage is an optimal arousal time for the individual; and outputting an indication to not wake the individual if it is not the optimal arousal time for the individual.

17. The method of claim 16, wherein the optimal arousal time for the individual is when the sleep stage is either stage 1 or stage 2 of non-rapid eye movement (NREM) sleep.

18. The method of claim 16, wherein the using the pressure data to determine a sleep stage includes extracting actigraphy data from the pressure data and filtering the actigraphy data to obtain respiration rates, wherein the respiration rates are used to determine the sleep stage.

19. The method of claim 16, further comprising:

monitoring the individual to determine oversleeping; and attempting to arouse the individual during the optimal arousal time when the individual is oversleeping.

20. A method, comprising:

receiving pressure data from at least one pressure sensor, wherein the at least one pressure sensor is associated with furniture used for an individual to sleep, wherein the device is adapted to set an adjustable trigger point of the at least one pressure sensor based on the individual's weight, the sensor's location on or in the furniture, or any combination thereof;

using the pressure data to determine a sleep stage for the individual;

using the determined sleep stage to determine whether the individual is in a negative state of wakefulness when the individual wakes from sleep;

detecting the individual entering one of one or more rooms of the individual's environment based on data received from an environmental sensor.

21. The method of claim 20, wherein the negative state of wakefulness is when the individual wakes from one of stages 3 and 4 of non-rapid eye movement (NREM) sleep and REM sleep stage.

22. The method of claim 20 further comprising causing a warning to the individual when the individual is in a negative state of wakefulness and is approaching a dangerous situation, wherein the dangerous situation is detected based on the data relating to the individual's environment.

23. A machine-readable medium containing instructions which, when executed by a processing system, cause the processing system to perform a method, the method comprising:

setting an adjustable trigger point of at least one pressure sensor associated with furniture used for an individual to sleep, the trigger point based on the individual's weight;

receiving pressure data from at least one pressure sensor;

using the pressure data to determine a sleep stage for the individual;

determining whether the sleep stage is an optimal arousal time for the individual; and outputting an indication to not wake the individual if it is not the optimal arousal time for the individual.

24. The machine-readable medium of claim 23, wherein the optimal arousal time for the individual is when the sleep stage is either stage 1 or stage 2 of non-rapid eye movement (NREM) sleep.

25. The machine-readable medium of claim 23, wherein the using the pressure data to determine a sleep stage includes extracting actigraphy data from the pressure data and filtering the actigraphy data to obtain respiration rates, wherein the respiration rates are used to determine the sleep stage.

26. The machine-readable medium of claim 23, further comprising:

monitoring the individual to determine oversleeping; and attempting to arouse the individual during the optimal arousal time when the individual is oversleeping.

* * * * *